United States Patent
Seifert (10) Patent No.: US 8,250,754 B2
(45) Date of Patent: Aug. 28, 2012

(54) METHOD OF MANUFACTURING A MEDICAL ELECTRICAL LEAD WITH INSERT-MOLDED ELECTRODE

(75) Inventor: Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 12/627,021

(22) Filed: Nov. 30, 2009

(65) Prior Publication Data

US 2010/0145423 A1    Jun. 10, 2010

Related U.S. Application Data

(60) Provisional application No. 61/118,606, filed on Nov. 29, 2008.

(51) Int. Cl.
*H01R 43/00* (2006.01)

(52) U.S. Cl. ............... 29/883; 29/860; 29/876; 607/119

(58) Field of Classification Search ............. 29/830, 29/857–860, 874, 876, 882, 883; 607/116, 607/119, 122

See application file for complete search history.

(56) References Cited

U.S. PATENT DOCUMENTS

| | | | |
|---|---|---|---|
| 4,481,953 A | 11/1984 | Gold et al. | |
| 4,603,705 A | 8/1986 | Speicher et al. | |
| 5,105,826 A | 4/1992 | Smits et al. | |
| 5,174,288 A | 12/1992 | Bardy et al. | |
| 5,271,417 A | 12/1993 | Swanson et al. | |
| 5,488,768 A * | 2/1996 | Mar | 29/860 |
| 5,522,872 A | 6/1996 | Hoff | |
| 5,676,694 A | 10/1997 | Boser et al. | |
| 5,728,149 A | 3/1998 | Laske et al. | |
| 5,928,277 A | 7/1999 | Laske et al. | |
| 5,935,159 A | 8/1999 | Cross, Jr. et al. | |
| 5,957,970 A | 9/1999 | Shoberg et al. | |
| 6,016,436 A | 1/2000 | Bischoff et al. | |
| 6,038,463 A | 3/2000 | Laske et al. | |
| 6,038,472 A | 3/2000 | Williams et al. | |
| 6,052,625 A | 4/2000 | Marshall | |
| 6,061,595 A | 5/2000 | Safarevich | |
| 6,181,971 B1 | 1/2001 | Doan | |
| 6,256,542 B1 | 7/2001 | Marshall et al. | |
| 6,259,954 B1 | 7/2001 | Conger et al. | |
| 6,289,251 B1 | 9/2001 | Huepenbecker et al. | |
| 6,615,695 B1 | 9/2003 | Hjelle et al. | |
| 6,697,675 B1 | 2/2004 | Safarevich et al. | |
| 6,704,604 B2 | 3/2004 | Soukup et al. | |
| 6,801,809 B2 | 10/2004 | Laske et al. | |
| 6,813,521 B2 | 11/2004 | Bischoff et al. | |
| 6,920,361 B2 | 7/2005 | Williams | |
| 7,031,777 B2 | 4/2006 | Hine et al. | |
| 7,130,700 B2 | 10/2006 | Gardeski et al. | |
| 7,277,762 B2 | 10/2007 | Belden et al. | |
| 7,474,924 B2 | 1/2009 | Honeck et al. | |
| 7,512,447 B2 | 3/2009 | Marshall et al. | |
| 2005/0240252 A1 | 10/2005 | Boser et al. | |
| 2007/0276458 A1 | 11/2007 | Boser | |
| 2009/0254162 A1 | 10/2009 | Quinci et al. | |

* cited by examiner

*Primary Examiner* — Donghai D. Nguyen (74) *Attorney, Agent, or Firm* — Reed A. Duthler (57) ABSTRACT

A medical electrical lead that includes a lead body and at least one tubular electrode sub-assembly positioned over and attached to the external surface of the lead body. The lead body includes at least one elongated conductive element, such as a cable, that is electrically connected to a coiled electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body which may potentially improve flexibility of the medical electrode lead in the area occupied by the tubular electrode sub-assembly.

19 Claims, 8 Drawing Sheets

METHOD OF MANUFACTURING A MEDICAL ELECTRICAL LEAD WITH INSERT-MOLDED ELECTRODE

CROSS-REFERENCE TO RELATED APPLICATIONS

This application claims the benefit of U.S. Provisional Application No. 61/118,606, filed on Nov. 29, 2008. The disclosure of the above application is incorporated herein by reference.

TECHNICAL FIELD

The disclosure relates to implantable medical devices and, more particularly, to implantable medical electrical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically include, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead can be inserted through various venous portions so that the tip portion can be positioned at the selected position near or in the muscle group. When therapy is required by a patient, the control module signals the battery to charge the capacitor, which in turn discharges electrical stimuli to tissue of a patient through via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module. In the context of implantable defibrillators, most systems include large surface area implantable electrodes to be mounted in or adjacent the heart.

One common approach of providing a large surface area electrode is to employ an elongated exposed coil of biocompatible metal. In the context of an endocardial lead, this is disclosed in U.S. Pat. No. 4,161,952 issued to Kinney. In the context of an epicardial lead, this is disclosed in the context of U.S. Pat. No. 4,817,634 issued to Holleman et al.

An elongated coil serving as the electrode is typically mounted around the exterior of an insulative lead body. It is believed desirable in this context to stabilize the electrode coil with respect to the lead body, both to provide mechanical integrity and to prevent fibrous ingrowth around the individual coils of the electrode coil. In the above cited Kinney et al. patent and in U.S. Pat. No. 4,934,049, issued to Keikhafer et al., this is accomplished by sliding the coil over the lead body and backfilling the spaces between the electrode coil with a plastic material. In prior U.S. Pat. Nos. 5,042,143 issued to Holleman, et al. and 5,344,708 issued to Bischoff, et al. alternative methods of producing a lead structure similar to that produced in the Keikhafer patent are disclosed. In these patents a plastic tube is stretched. An electrode coil having a inner is then slid over the stretched tube, after which the tube, after which the tube is released, allowing it to return to its previous length. Thereafter, a mandrel is inserted into the tubing, compressing the tubing between the mandrel and the conductor coil. The assembly is thereafter heated, allowing the tubing to flow into spaces between the electrode coil to a desired depth.

U.S. patent application Ser. No. 11/549,284 filed Oct. 13, 2006 by Boser also discloses mechanisms for producing leads employing such electrode

SUMMARY OF THE INVENTION

The present disclosure relates to medical electrical leads that include a lead body and at least one tubular electrode sub-assembly positioned over and attached to the external surface of the lead body. The lead body includes at least one elongated conductive element, such as a cable, that is electrically connected to a coiled electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body which may potentially improve flexibility of the medical electrode lead in the area occupied by the tubular electrode sub-assembly.

The tubular electrode sub-assemblies may include an organic polymeric tubular liner comprising an outer surface and a continuous, uninterrupted inner surface that extends from between a proximal end and distal end of the tubular liner, and an electrode embedded in the outer surface of the polymeric tubular liner, wherein at least a portion of an outer surface of the electrode comprises an exposed outer surface proximate an outer surface of the polymeric tubular liner, and wherein the liner extends into interstices of the electrode.

The medical electrical lead may include one or more selected attachment sites at which the tubular electrode sub-assembly is attached to the external surface of the lead body, wherein the one or more selected attachment sites occupy only a portion of the inner surface of the polymeric tubular liner; and an electrical connection within the medical electrode lead between the electrode and the conductive element.

The present disclosure also relates to methods of manufacturing medical electrical leads that include manufacturing a tubular electrode sub-assembly by masking an outer surface of an electrode with a masking structure provided over the outer surface of the electrode, delivering a flowable liner material comprising a hardenable organic polymer into an interior of the electrode while masking the outer surface of the electrode with the masking structure, wherein the flowable liner material fills interstices of the electrode and forms an outer liner surface proximate the masking structure, removing a portion of the flowable liner material from the interior of the electrode by inserting a mandrel into the interior of the electrode; hardening the flowable liner material to form a hardened liner material after inserting the mandrel into the interior of the electrode, removing the mandrel from the interior of the electrode after hardening the flowable liner material, wherein the hardened liner material forms an inner liner surface within the interior of the electrode, and removing the masking structure from the outer surface of the electrode after hardening the flowable liner material, wherein the hardened liner material forms an outer liner surface in the interstices of the electrode, and wherein the masked portion of the outer surface of the electrode is exposed after removing the masking structure.

The method of manufacturing a lead may further include positioning the tubular electrode sub-assembly over an external surface of a lead body after manufacturing the tubular electrode sub-assembly such that the inner liner surface faces the external surface of the lead body, wherein the lead body defines a longitudinal axis extending between a proximal end and a distal end of the lead body, and wherein the longitudinal axis extends through the tubular electrode sub-assembly; attaching the tubular electrode sub-assembly to the external surface of the lead body at one or more selected attachment sites, wherein the one or more selected attachment sites occupy only a portion of an inner liner surface; and electrically connecting a conductive element located within an interior of the lead body to the coiled electrode of the tubular electrode sub-assembly.

The principles described herein are applicable to all types of medical electrical leads. For example, the disclosure applies to cardiovascular leads (e.g. high voltage leads, low voltage leads etc.), neurological leads, or other suitable applications. Also, although described with respect to coiled electrodes, other electrode configurations may alternatively be used.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following detailed description, reference is made to the accompanying figures of the drawing which form a part hereof, and in which are shown, by way of illustration, specific embodiments. It is to be understood that other embodiments may be utilized and structural changes may be made without departing from the scope of the present disclosure.

Figure 1:
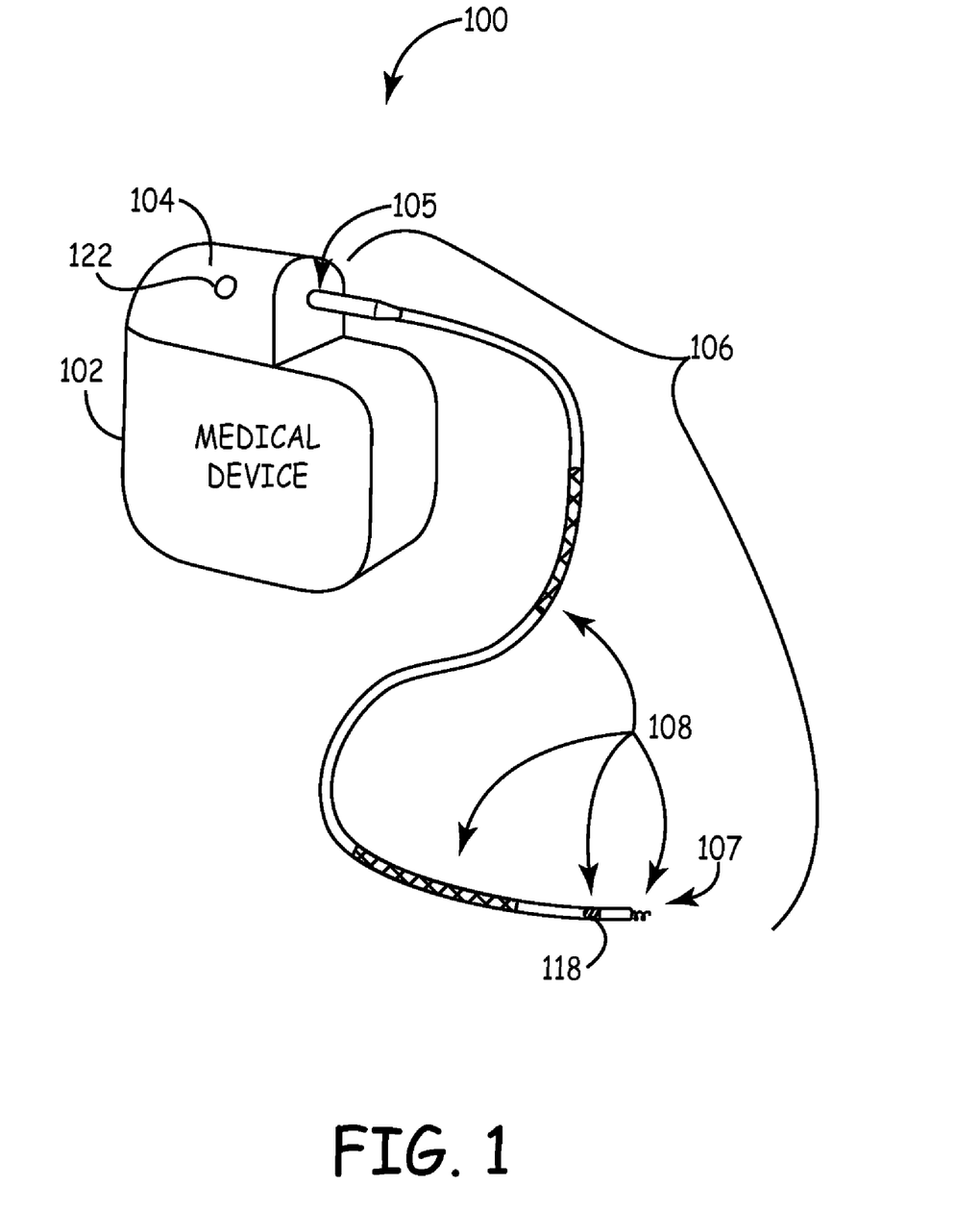
FIG. 1 is a conceptual schematic view of an implantable medical device in which a medical electrical lead extends therefrom.

FIG. 1 depicts a medical device system 100. A medical device system 100 includes a medical device housing 102 having a connector module 104 (e.g. international standard (IS)-1, defibrillation (DF)-1, IS-4 etc.) that electrically couples various internal electrical components housed in medical device housing 102 to a proximal end 105 of a medical electrical lead 106. A medical device system 100 may comprise any of a wide variety of medical devices that include one or more medical lead(s) 106 and circuitry coupled to the medical electrical lead(s) 106. An exemplary medical device system 100 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIRTUOSOT™, RESTORE™, RESTORE ULTRA™, sold by Medtronic, Inc. of Minnesota. Non-implantable medical devices or other types of devices may also utilize batteries such as external drug pumps, hearing aids and patient monitoring devices or other suitable devices. Medical device system 100 may deliver, for example, pacing, cardioversion or defibrillation pulses to a patient via electrodes 108 disposed on distal end 107 of one or more lead(s) 106. Specifically, lead 106 may position one or more electrodes 108 with respect to various cardiac locations so that medical device system 100 can deliver electrical stimuli to the appropriate locations.

Figure 2:
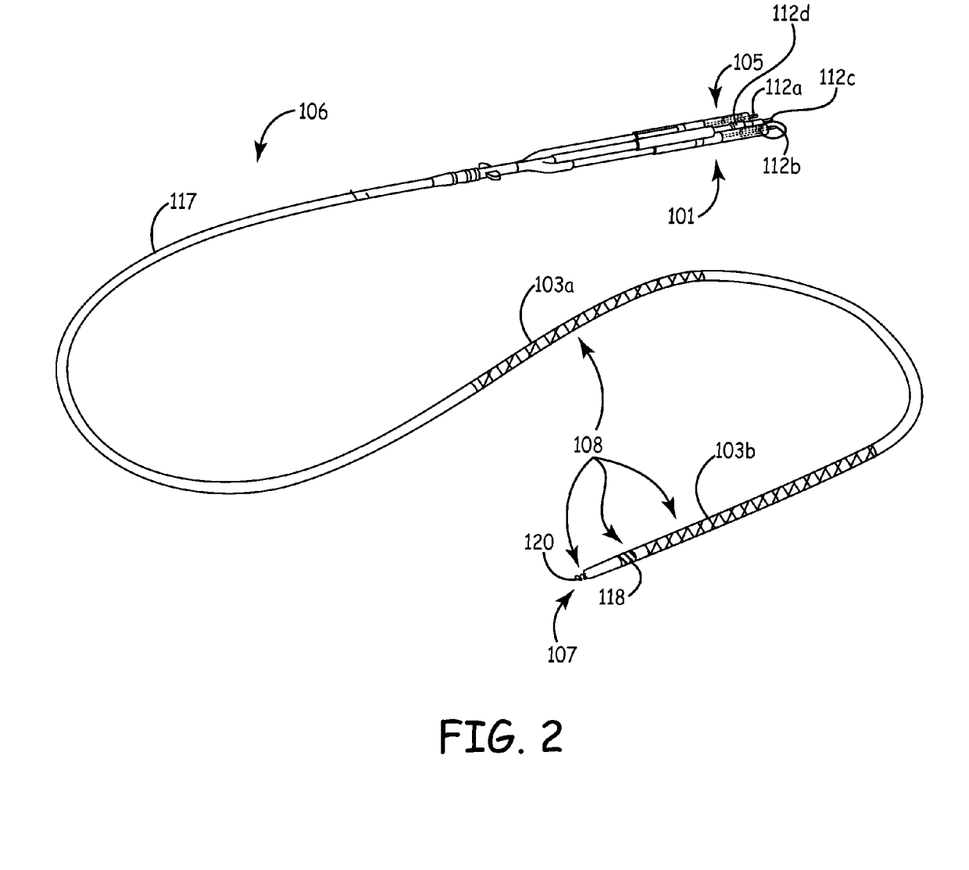
FIG. 2 is a schematic view of a medical electrical lead.

FIG. 2 depicts lead 106. Lead 106 includes a lead body 117 that extends from proximal end 105 to a distal end 107. Lead body 117 can include one or more connectors 101, and one or more jacketed conductive elements 112a-d. A jacket (also referred to as a liner, longitudinal element, coating) extends along and longitudinally around the conductive elements 112a-d and can serve to contain or mechanically constrain one or more conductive elements 112a-d. A jacket can also insulate one or more conductive elements 112a-d. Connector module 104 can contain connectors 122, such as set screws, serve to electrically and mechanically connect conductive elements 112a-d to ports (not shown) of connector module 104. Conductive element 112c (also referred to as a "conductor coil," torque coil", "distal tip conductor") can extend to the distal end 107 and can optionally be coupled to a retractable and/or extendable helical tip. One or more conductive elements 112a,b serve as, or are connected to, defibrillation coils 103a,b that deliver electrical stimuli, when necessary, to tissue of a patient. Lead 106 can also include a conductive element 112d that extends from the proximal end 105 to ring electrode 118 while another conductive element 112c extends from proximal end 105 to tip electrode 120.

Electrically conductive elements that extend along the length of the lead 106 can include coils, wires, coil wound around a filament, cables, conductors or other suitable members. Conductive elements can include platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. The electrically conductive elements are typically covered, or substantially covered, longitudinally with a jacket. In yet another embodiment, each conductive element within the lead body 117 is surrounded by a tubular element within the jacket, which can possess a circular or a non-circular cross-section. Any or all of the components within the lead body 117 can exhibit a non-circular cross-section.

Typically, the outer surface of electrodes 108 such as the ring electrode 118, the tip electrode 120, and the defibrillation electrodes 103a,b are exposed or not covered by a jacket or liner so that electrodes 108 can sense and/or deliver electrical stimuli to tissue of a patient. A sharpened distal tip (not shown) of tip electrode 120 may facilitate fixation of the distal end of helically shaped tip electrode 120 into tissue of a patient.

Figure 3A:
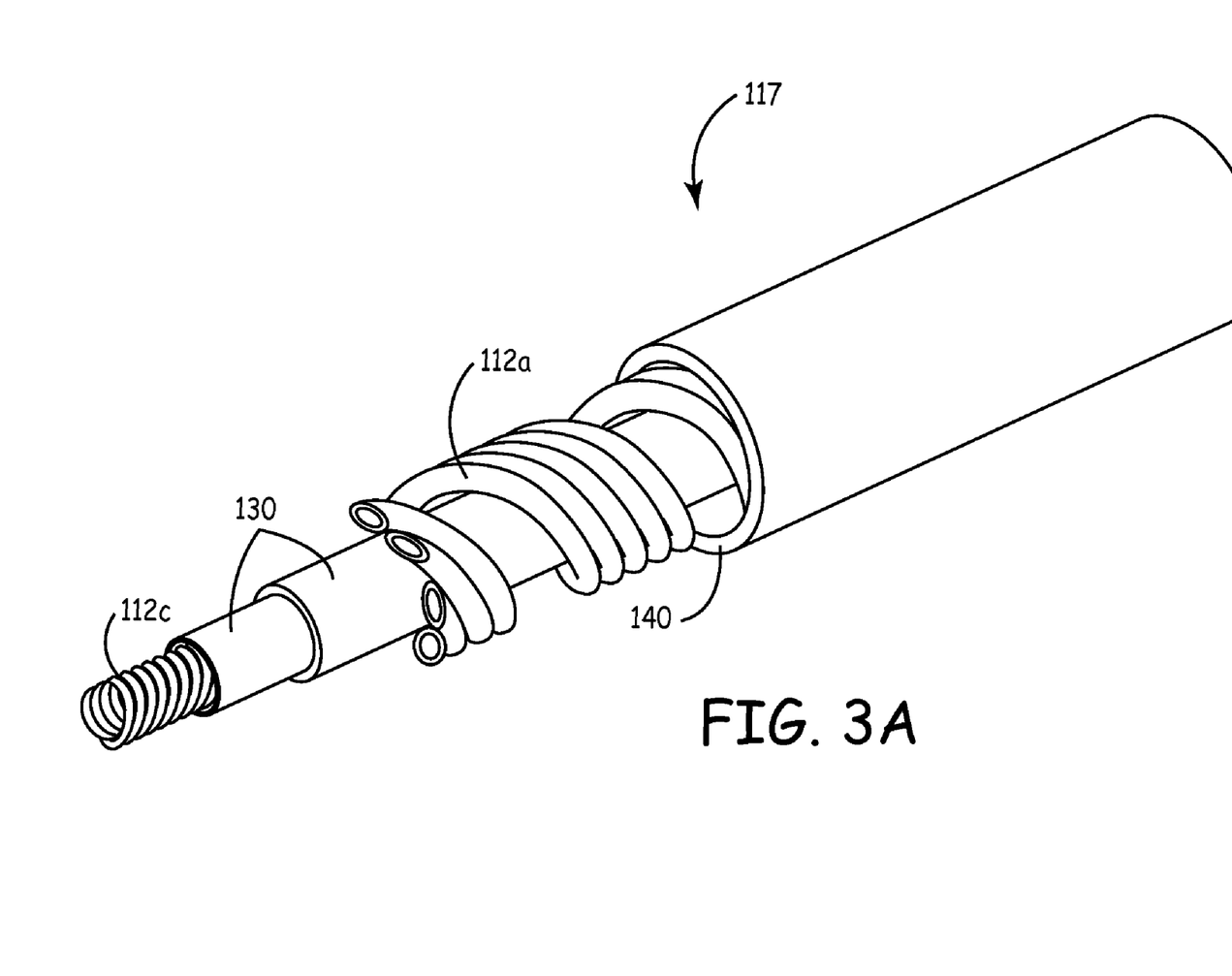
FIG. 3A and FIG. 3B are schematic views of a distal end of the medical electrical lead.
Figure 3B:
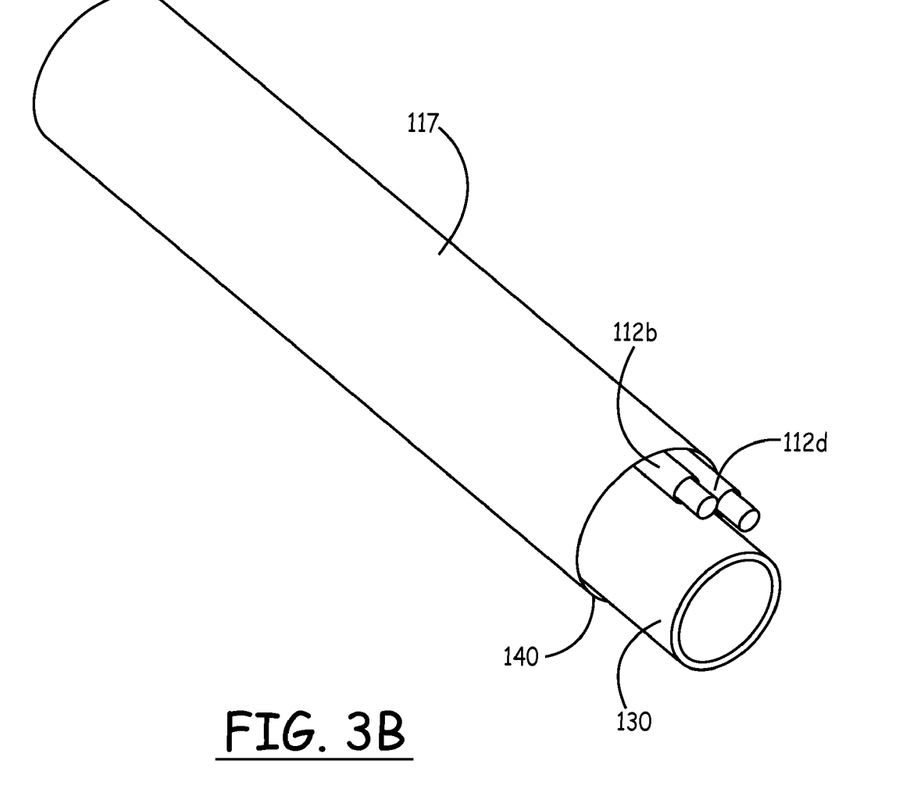

FIGS. 3A and 3B depict to examples of lead bodies that may be used in connection with the medical electrical leads of the present disclosure. Referring to FIG. 3A, one example of a lead body 117 is depicted that includes one or more conductive elements 112a and 112c that are provided in a wrapped configuration. The depicted lead body 117 also includes comprises one or more internal jackets 130 with an outer jacket 140 that surrounds the one or more internal jackets 130. FIG. 3B depicts another lead body that includes one or more conductive elements 112b and 112d that extend linearly along the length of the lead body 117. The conductive elements 112b and 112d may be located between an inner structure 130 and an outer jacket 140. In some embodiments, both wrapped and linear conductive elements may be provided in the same lead body. In another embodiment (not pictured) of a lead body that may be used is a multi-lumen tubular structure (symmetric or asymmetric).

Among the electrodes 108, some of the electrodes, such as defibrillation electrodes 103a and 103b, may be provided in the form of coiled electrodes that form a helix, while other electrodes may be provided in different forms. Further, some of the electrodes 108 may be provided in the form of tubular electrode sub-assemblies that can be pre-fabricated and positioned over an existing lead body, where they are attached and where electrical connections with conductive elements within the lead body 117 can be made.

Figure 4:
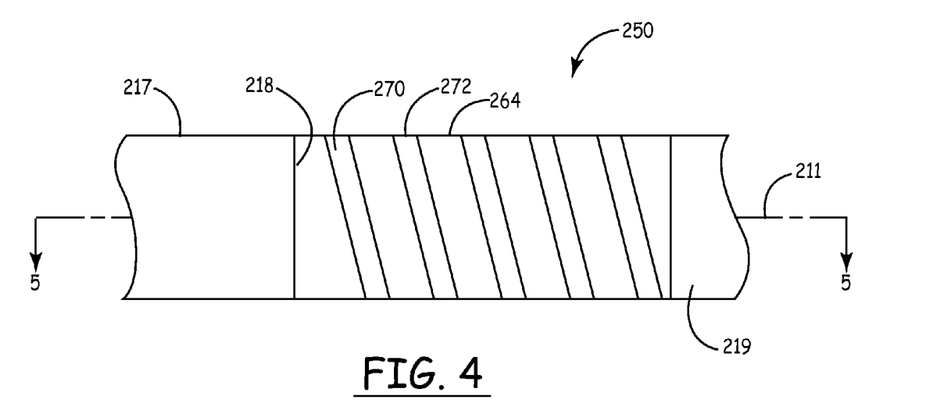
FIG. 4 is a schematic view of a portion of the medical electrical lead that includes a tubular electrode assembly attached thereto.
Figure 5:
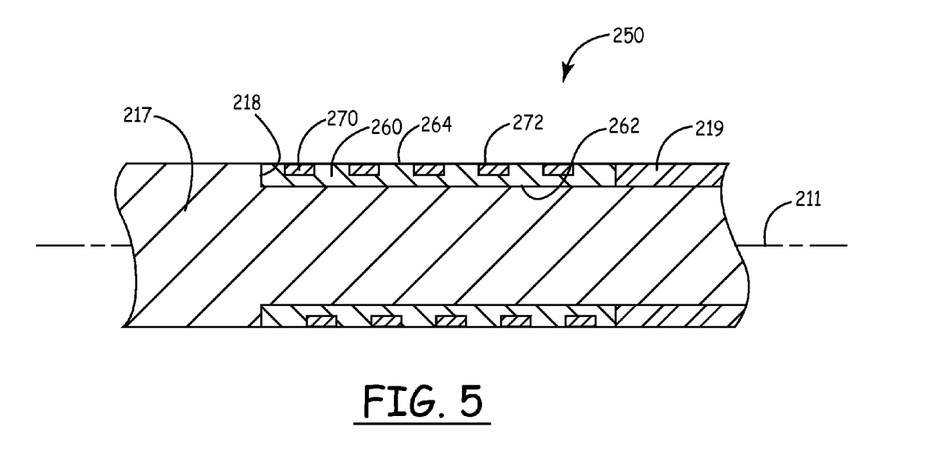
FIG. 5 is a schematic sectional view of the portion of the medical electrical lead of FIG. 4, taken along line 5-5 in FIG. 4.

An example of one such tubular electrode sub-assembly 250 is depicted in FIGS. 4 and 5, where the tubular electrode sub-assembly 250 is positioned over a portion of a lead body 217. The tubular electrode sub-assembly 250 includes a tubular liner 260 and electrode 270 embedded in the outer surface 264 of the tubular liner 260. The electrode 270 is preferably embedded in the outer surface 264 of the tubular liner 260 to a depth that is sufficient to mechanically couple the electrode 270 to the tubular liner 260. At least a portion of the outer surface 272 of the electrode 270 is exposed proximate the outer surface 264 of the tubular liner 260 such that the electrode 270 can be placed in electrical communication with tissue and/or fluids surrounding the tubular electrode sub-assembly 250.

Another optional feature depicted in FIGS. 4 and 5 is that the lead body 217 may be constructed with a variable diameter such that the area in which the tubular electrode sub-assembly 250 is positioned has a reduced size as compared to other portions of the lead body 217. For example, the lead body 217 may include a shoulder 218 as seen in FIG. 5 where the size of the lead body 217 decreases. The diameter of the lead body 217 may be increased on the opposite end of the tubular electrode sub-assembly 250 by optionally including a sleeve 219 or other structure to increase the size of the lead. Such a construction can be used to provide an isodiametric lead, although other constructions could also be used to compensate for the thickness of the tubular electrode sub-assembly 250.

The electrode 270 may, in some embodiments, be formed in the shape of a coil with one or more wraps or coils and using a wire element having a rectangular cross-section as depicted in FIG. 5, although coiled electrodes in other embodiments may be formed using wire elements having any selected shape (e.g., round, oval, elliptical, etc.).

The tubular liner 260 may be located between the electrode 270 and the underlying structure of the lead body 217 over a majority of the inner surface 262 of the tubular liner 260. Exceptions to this may occur where, for example, the electrode is connected to a conductive element extending through the lead body 217. That electrical connection may be made by a variety of techniques, with at least some potentially suitable connection techniques being described in US Patent Application Publication Nos. US 2005/0240252 (Boser et al.); US 2005/0113898 (Honeck et al.); etc.

The tubular liner 260 may alternatively be characterized as preventing contact between the inner surface of the electrode and the underlying structure of the lead body 217 (except where electrical connections may need to be made as described above).

In yet another manner of characterizing the relationship between the tubular liner 260 and the electrode 270 in some embodiments, the tubular liner 260 can be described as optionally having a liner thickness measured radially from the longitudinal axis 211 between the inner surface 262 and the outer surface 264 of the tubular liner 260. The electrode 270 can be described as having an electrode thickness that is measured radially from the longitudinal axis 211. Further, the liner thickness may be greater than the electrode thickness in some embodiments (as depicted, e.g., in FIG. 5).

The tubular liner 260 includes an inner surface 262 that faces the underlying structure of the lead body 217. The tubular electrode sub-assembly 250 is preferably attached to underlying structure of the lead body 217 at one or more selected attachment sites. As discussed herein, the one or more selected attachment sites preferably occupy only a portion of the inner surface 262—in some embodiments, the selected attachment sites may be described as occupying no more than about 50% of the inner surface 262 of the tubular liner 260. By limiting the surface area of attachment between the tubular electrode sub-assembly 250 and the underlying structure of the lead body 217, flexibility of the lead may be improved as compared to a lead in which the entire tubular electrode sub-assembly 250 was attached to the underlying structure of the lead body 217.

Figure 6A:
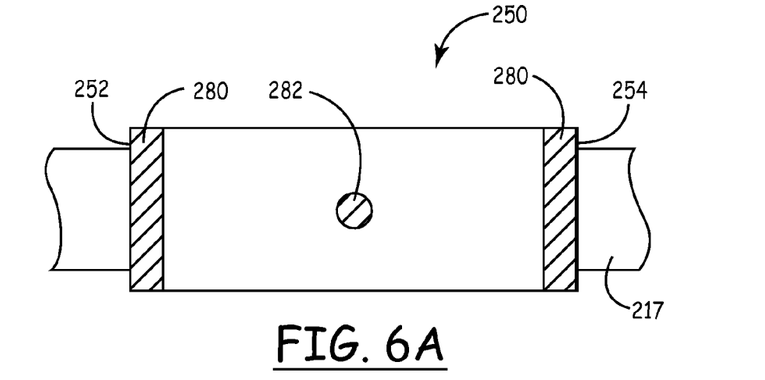
FIG. 6A is a schematic view of a portion of a medical electrical lead including markings to show one arrangement of selected attachment sites where the tubular electrode sub-assembly is attached to the lead body.
Figure 6B:
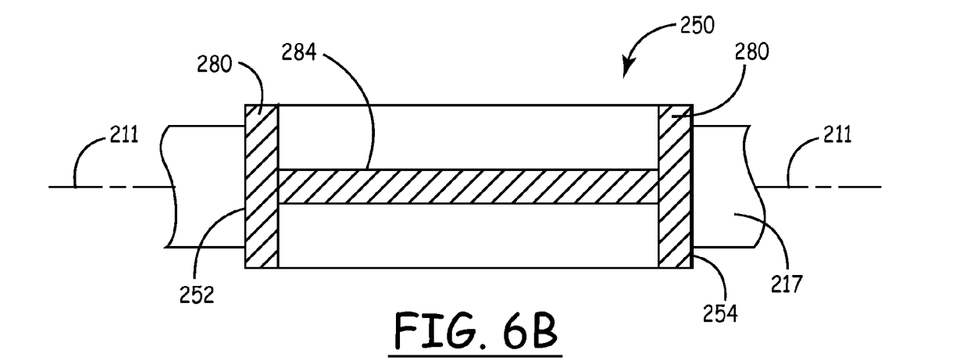
FIG. 6B is a schematic view of a portion of another medical electrical lead including markings to show an alternative arrangement of selected attachment sites where the tubular electrode sub-assembly is attached to the lead body.
Figure 6C:
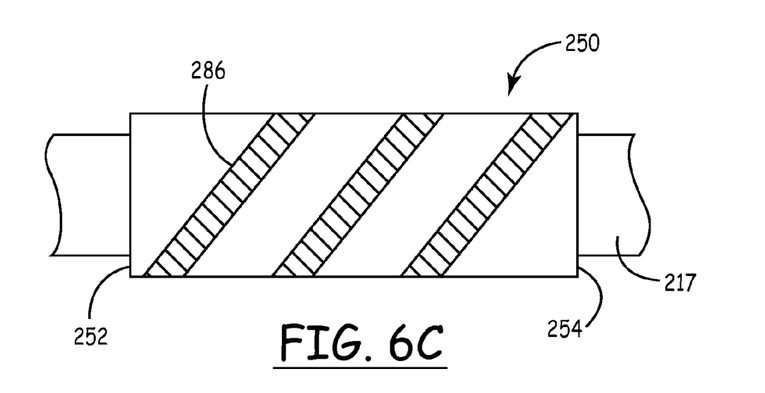
FIG. 6C is a schematic view of a portion of another medical electrical lead including markings to show an alternative arrangement of selected attachment sites where the tubular electrode sub-assembly is attached to the lead body.

FIGS. 6A-6C depict only some of the potentially infinite variations in selection and arrangement of selected attachment sites that may be used to attach the tubular electrode sub-assembly 250 to the underlying lead body 217. The coiled electrode and other features are not depicted in FIGS. 6A-6C for clarity.

In FIG. 6A, the tubular electrode sub-assembly 250 may be attached at its proximal end 252 and its distal end 254 by selected attachment sites 280 that may be in the form of rings around the tubular electrode sub-assembly 250. Although the selected attachment sites 280 at the proximal and distal ends are depicted as continuous rings, they may be provided in any other form, e.g., a group of discrete attachment sites that are arranged around the periphery of the tubular electrode sub-assembly 250 such that a ring structure is formed, etc.

The set of selected attachment sites depicted in FIG. 6A may also optionally include one or more intermediate selected attachment sites 282 positioned between the proximal end 252 and the distal end 254 of the tubular electrode sub-assembly 250. Such an intermediate selected attachment site 282 may be provided in combination with attachment sites 280 at the ends of the tubular electrode sub-assembly 250 or one or more intermediate selected attachment sites 282 may be provided in the absence of attachment sites at the ends of the tubular electrode sub-assembly 250.

One potential alternative arrangement of selected attachment sites is depicted in FIG. 6B in which a selected attachment site 284 in the form of a line is depicted in combination with selected attachment sites 280 at the ends of the tubular electrode sub-assembly 250. Although depicted as a straight line that extends from the proximal end 252 to the distal end 254 of the tubular electrode sub-assembly 250 and that is aligned with the longitudinal axis 211, the line 284 may be shorter and/or the line 284 may not be aligned with the longitudinal axis 211. Further, the attachment site 284 may be provided in combination with attachment sites 280 at the ends of the tubular electrode sub-assembly 250 (as depicted) or one or more such lines may be provided in the absence of attachment sites at the ends of the tubular electrode sub-assembly 250.

Another potential alternative arrangement of selected attachment sites is depicted in FIG. 6C in which a selected attachment site 286 is provided in the form of a helix that extends around the tubular electrode sub-assembly 250 and proceeds along its length between the proximal end 252 and the distal end 254. Although the selected attachment site 286 is depicted as a continuous structure, it may be provided in any other form, e.g., a group of discrete attachment sites that are arranged around and along the tubular electrode sub-assembly 250 such that a helical structure is formed, etc. Additional selected attachment sites may also be provided in combination with a helical selected attachment site 286.

In still another alternative, limiting the area occupied by the attachment sites between the tubular electrode sub-assembly 250 and the underlying structure of the lead body may not be used if, for example, the tubular electrode sub-assembly 250 is attached to the underlying structure of the lead body by an attachment agent that has a lower modulus than the material used to construct the liner 260 of the tubular electrode sub-assembly 250. For example, using a silicone medical adhesive to attach the inner surface of the liner 260 to the underlying structure of the lead body 217 may provide sufficient compliance to provide enhanced flexibility in the lead such that the attachment agent (e.g., silicone adhesive, etc.) may occupy more than about 50% of the surface are occupied by the tubular electrode sub-assembly 250. In some embodiments, the attachment agent may be provided over substantially all of the interface between the inner surface of the liner 260 and the underlying structure of the lead body 217.

As discussed herein, the electrode 270 is embedded in the outer surface 264 of the tubular liner 260. One potential method for manufacturing a tubular electrode sub-assembly having such a construction is depicted and will be described in connection with FIGS. 7A-7D, which are sectional views taken during different stages of the manufacturing process.

Figure 7A:
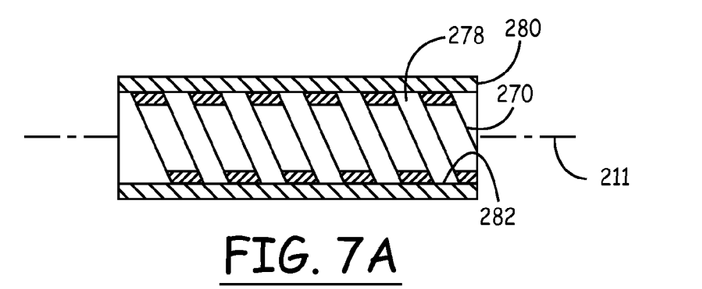
FIG. 7A is a schematic sectional view of a process for forming a tubular electrode sub-assembly with an insert-molded coiled electrode in which the electrode is contained within a masking structure.

The process begins with an electrode 270 which is located within a masking structure 280. The masking structure 280 preferably masks the outer surface of the electrode 270 such that the flowable liner material is inhibited from coating the outer surface of the electrode 270. Although the electrode 270 has a flat outer surface, in some embodiments the electrode may have a more complex outer surface if, e.g., the coils are formed using round wires or wires with other cross-sectional shapes. In such embodiments, it may be helpful if the masking structure can at least partially conform to such surface such that larger portions of the outer surface are masked. The masking structure 280 may be provided in the form of a tube, although tapes, sheets and other structures could potentially be used. Alternatively, the masking structure may take the form of a mold cavity appropriately shaped to conform to portions of the outer surface.

In one embodiment, the masking structure 280 may be in the form of a heat-shrinkable tube that is placed over the electrode 270 and then heated such that the tube diameter decreases to compress the outer surface of the electrode 270. One example of this is depicted in FIG. 7A, where masking structure 280 may be in the form of a heat-shrinkable tubing that has been shrunk to mask the outer surface of the electrode 270. In addition to masking the outer surface of the electrode 270, the masking structure 280 may also function as a mold or containment structure for the liner material in the interstices 278 of the coiled electrode 270. Further, the heat shrink tubing may conform to the shape of the outer surface of the electrode even if that outer surface is not flat, e.g., if the electrode 270 is constructed with a rounded wire or wire having an outer surface that is not flat.

With the masking structure 280 in place, a flowable liner material 266 can be delivered into the interior of the electrode 270 such that the flowable liner material fills the interstices 278 of the electrode 270 (e.g., between adjacent coils of a coiled electrode) and forms an outer liner surface proximate the inner surface 282 of the masking structure 280. The flowable liner material may be delivered into the interior of the coiled electrode by any suitable technique, e.g., a syringe, extrusion nozzle, etc.

Figure 7B:
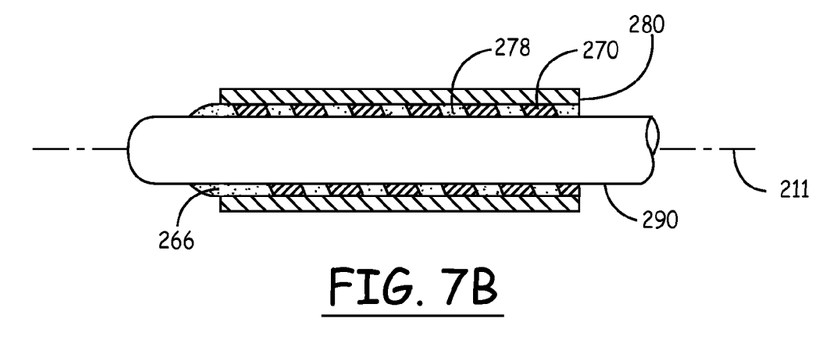
FIG. 7B is a schematic sectional view of FIG. 7A after the interior of the electrode has been filled with flowable liner material and a mandrel has been inserted through the electrode.

With the flowable liner material 266 in place in the coiled electrode 270, at least a portion of the flowable material may be removed by inserting a mandrel 290 into the interior of the coiled electrode as depicted in FIG. 7B. The mandrel 290 may be solid or hollow, although one embodiment of the mandrel 290 may be in the form of a hollow tube. The mandrel may be made of metal, such as annealed copper wire or silver-plated copper wire, for example. A metal-containing mandrel may be coated with an organic polymer to facilitate release from the liner. Such coating materials include PTFE-based coatings, polyimide, or other polymeric coatings such as "PD Slick" coating materials. Alternatively, the mandrel may be made of a polymeric material. In one embodiment of the mandrel 290 may be in the form of a hollow polymeric tube. Polymers for such a mandrel 290 may be, e.g., ethylene tetrafluoroethylene (ETFE), polytetrafluoroethylene (PTFE), or fluorinated ethylene propylene (FEP).

After the mandrel 290 is in place, the flowable liner material 266 may be limited to the interstices 278 between adjacent coils of the electrode 270 as depicted in FIG. 7B, although a portion of the liner material 266 may remain between the mandrel 290 and the inner surface of the coiled electrode 270.

The flowable liner material 266 may then be hardened (for example, by curing (e.g., crosslinking), removing solvent, or cooling) while the mandrel 290 is located within the interior of the electrode 270 such that the liner material forms a liner 260 that is located at least between the interstices 278 of the electrode 270.

Figure 7C:
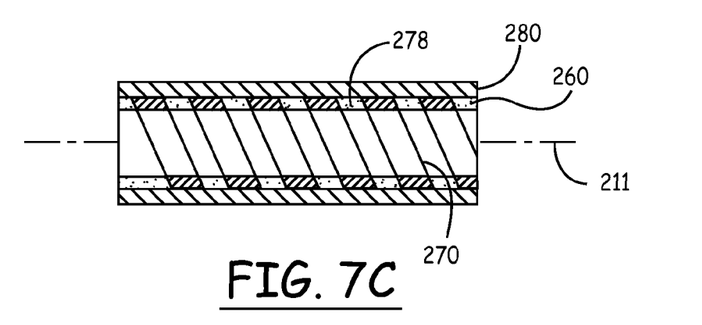
FIG. 7C is a schematic sectional view of FIG. 7B after the liner material is hardened and the mandrel has been removed from the interior of the electrode.

After the liner material 266 hardened, the mandrel 290 can be removed and excess liner material removed such that the structure depicted in FIG. 7C is provided which includes the electrode 270 surrounded by the masking structure 280, with the liner material forming a liner 260 that fills the interstices 278 in the electrode 270 and that may also be found in a relatively thin layer on the inner surface of the electrode 270.

The mandrel removal may be accomplished by a variety of techniques that may include, e.g., deformation, dissolution, etc. If the mandrel 290 is, e.g., a structure that necks down when elongated along the axis 211, then the removal process may involve stretching the mandrel 290 along the axis 211 such that it necks down. The mandrel 290 may be made of material that releases cleanly from the material of the liner 260.

Figure 7D:
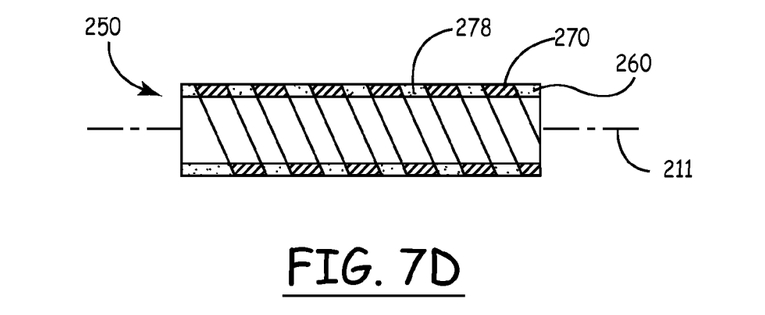
FIG. 7D is a schematic sectional view of the resulting tubular electrode sub-assembly 250 after the masking structure has been removed from the outer surface of the electrode, wherein the liner material forms the liner 260.
Figure 8:
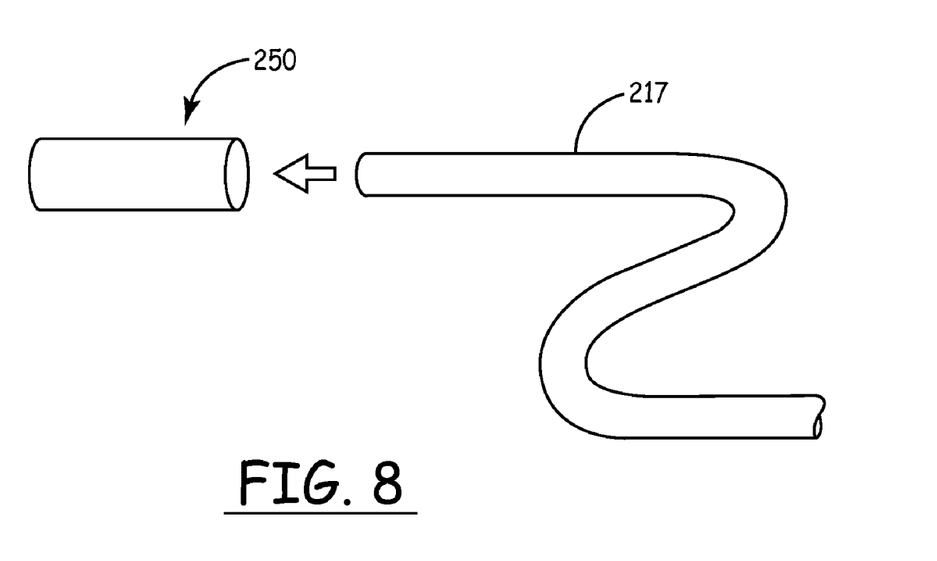
FIG. 8 is a schematic view of a process for placing a tubular electrode sub-assembly onto a lead body.

After the masking structure 280 is removed from the coiled electrode 270 and the liner 260, the finished tubular electrode sub-assembly 250 is obtained as depicted in FIG. 7D. Further processing may potentially be performed to place the tubular electrode sub-assembly 250 in condition to be placed over a lead body as depicted in FIG. 8 and attached thereto in one or more selected attachment sites as described herein. Such processing to prepare the tubular electrode sub-assembly 250 for attachment to a lead body 217 may include, trimming the tubular electrode sub-assembly 250 to a selected length, preparing the ends or other portions of the coiled electrode for attachment to a conductive element within the lead body 217, etc.

Attachment of the tubular electrode sub-assembly 250 to a lead body 217 may be accomplished using any suitable technique or combination of techniques. In some embodiments, the tubular electrode sub-assembly 250 may be attached to the lead body 217 by welding or fusing the material of the liner 260 to the lead body 217. Such welding or fusing may be performed using any suitable technique or combination of techniques, e.g., ultrasonically, thermally, chemically (using, e.g., solvents), etc.

Another potential technique for providing the selected attachment sites between the tubular electrode sub-assembly 250 and the lead body 217 may be through the use of adhesive. Exemplary adhesive may include silicones, urethanes, fluoropolymers etc. The adhesives could include those activated via thermal, UV light, chemical, moisture, and solvent-based methods.

Another potentially optional additional process that may be used is to backfill or overcoat the tubular electrode sub-assembly 250 to fill any gaps between the liner and the electrode before and/or after positioning it on a medical electrical lead with a hardenable organic polymeric material that has a relatively low modulus (i.e., low stiffness, low durometer) for good flexibility of the final assembly, and has a relatively low viscosity (e.g., "pre-cure" viscosity) for good mold-filling properties. The material used to backfill may be a thermoset or a thermoplastic material. Examples include silicones, polyimides, epoxies, polyurethanes, polyurethanes with surface-modifying end groups (SME), polyurethane silicone block copolymers (e.g., a thermoplastic silicone polyether urethane available under the designation PurSil), ethylene tetrafluoroethylene (ETFE), polytetrafluoroethylene (PTFE), polyvinylidine difluoride (PVDF), Dyneon's THV (a polymer of tetrafluoroethylene, hexafluoropropylene and vinylidene fluoride), Daikin's T-530 fluoroelastomer, and other fluoropolymers and fluoropolymer elastomers, polyethylenes, and polyesters.

The flowable liner materials used to form the liners of the tubular electrode sub-assemblies of the present disclosure may be selected from any suitable hardenable organic polymeric material that has a relatively low modulus (i.e., low stiffness, low durometer) for good flexibility of the final assembly, and has a relatively low viscosity (e.g., "pre-cure" viscosity) for good mold-filling properties. The flowable liner materials may be formed of a thermoset or a thermoplastic material that can be extruded or processed into a tube. Examples include silicones, polyimides, epoxies, polyurethanes, polyurethanes with surface-modifying end groups (SME), polyurethane silicone block copolymers (e.g., a thermoplastic silicone polyether urethane available under the designation PurSil), fluoropolymers and fluoroelastomers (e.g., ethylene tetrafluoroethylene (ETFE), polytetrafluoroethylene (PTFE), polyvinylidine difluoride (PVDF), Dyneon's THV (a polymer of tetrafluoroethylene, hexafluoropropylene and vinylidene fluoride), Daikin's T-530 fluoroelastomer, and other fluoropolymers and fluoroelastomers), polyethylenes, and polyesters.

In some embodiments, a thermoset material, such as low consistency silicones (e.g., those available under the trade designations MED-4719 or MED-4755 from NuSil), liquid silicone rubber (LSR) (such as Dow Corning's Q7-4850 or NuSil's MED-4850), and "SI polyimide" as described in U.S. Pat. No. 5,639,850 and U.S. Pat. Pub. No. 2005/0004643 (para 17), can be used for the liner materials. In some embodiments, a thermoplastic material, such as a polyurethane silicone block copolymer (such as PurSil silicone polyether urethane), a polyurethane, a polyurethane with surface-modifying end groups, and ETFE), can be used for the liner materials.

The electrodes used in the tubular electrode assemblies may be selected from a wide variety of electrically conductive biocompatible materials (including, but not limited to, titanium, stainless steel, tantalum, platinum, etc. and combinations thereof (e.g., platinum-iridium clad tantalum, etc.)) that can be formed to take on any selected shape, e.g., a coiled helical shape, etc.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a leg clamp may refer to one or more leg clamps unless otherwise indicated.

The term "and/or" means one or all of the listed elements or a combination of any two or more of the listed elements.

The complete disclosure of the patents, patent documents, and publications identified herein are incorporated by reference in their entirety as if each were individually incorporated.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A method of manufacturing a medical electrical lead, the method comprising:

manufacturing a tubular electrode sub-assembly by:

masking an outer surface of an electrode with a masking structure provided over the outer surface of the electrode, delivering a flowable liner material comprising a hardenable organic polymer into an interior of the electrode while masking the outer surface of the electrode with the masking structure, wherein the flowable liner material fills interstices of the electrode and forms an outer liner surface proximate the masking structure, removing a portion of the flowable liner material from the interior of the electrode by inserting a mandrel into the interior of the electrode;

hardening the flowable liner material to form a hardened liner material after inserting the mandrel into the interior of the electrode, removing the mandrel from the interior of the electrode after hardening the flowable liner material, wherein the hardened liner material forms an inner liner surface within the interior of the electrode, removing the masking structure from the outer surface of the electrode after hardening the flowable liner material, wherein the hardened liner material forms an outer liner surface in the interstices of the electrode, and wherein the masked portion of the outer surface of the electrode is exposed after removing the masking structure;

positioning the tubular electrode sub-assembly over an external surface of a lead body after manufacturing the tubular electrode sub-assembly such that the inner liner surface faces the external surface of the lead body, wherein the lead body defines a longitudinal axis extending between a proximal end and a distal end of the lead body, and wherein the longitudinal axis extends through the tubular electrode sub-assembly;

attaching the tubular electrode sub-assembly to the external surface of the lead body at one or more selected attachment sites, wherein the one or more selected attachment sites occupy only a portion of an inner liner surface; and electrically connecting a conductive element located within an interior of the lead body to the electrode of the tubular electrode sub-assembly.

2. The method of claim 1, wherein the masking structure compresses against the outer surface of the electrode.

3. The method of claim 1, wherein the masking comprises shrinking a heat shrinkable tubing over the outer surface of the electrode.

4. The method of claim 1, wherein removing the mandrel comprises deforming the mandrel.

5. The method of claim 1, wherein removing the mandrel comprises stretching the mandrel along an axis extending through the interior of the electrode.

6. The method of claim 5, wherein the mandrel comprises a polymeric mandrel.

7. The method of claim 1, wherein the liner material is located between the electrode and the underlying structure of the lead body over a majority of the underlying structure of the lead body covered by the tubular electrode sub-assembly.

8. The method of claim 1, wherein the liner material prevents contact between an inner surface of the electrode and the underlying structure of the lead body.

9. The method of claim 1, wherein the liner material in the interstices of the electrode has a liner thickness measured radially from the longitudinal axis between the inner liner surface and the outer liner surface, and wherein the electrode has an electrode thickness measured radially from the longitudinal axis, and further wherein the liner thickness is greater than the electrode thickness.

10. The method of claim 1, wherein the one or more selected attachment sites comprise a proximal end and a distal end of the tubular electrode sub-assembly.

11. The method of claim 1, wherein the one or more selected attachment sites comprise a proximal end of the tubular electrode sub-assembly, a distal end of the tubular electrode sub-assembly, and an intermediate location between the proximal end and the distal end of the tubular electrode sub-assembly.

12. The method of claim 1, wherein the one or more selected attachment sites occupy no more than about 50% of the inner liner surface.

13. The method of claim 1, wherein at least one selected attachment site of the one or more selected attachment sites is in the form of a line extending along at least a portion of a length of the tubular electrode sub-assembly between a proximal end and a distal end of the tubular electrode sub-assembly.

14. The method of claim 13, wherein the line extends from the proximal end of the tubular electrode sub-assembly to the distal end of the tubular electrode sub-assembly.

15. The method of claim 13, wherein the line is aligned with the longitudinal axis.

16. The method of claim 13, wherein the line comprises a helix formed around the longitudinal axis.

17. The method of claim 1, wherein the flowable liner material comprises a hardenable organic polymeric material selected from the group consisting of polyurethanes, polyurethanes with surface-modifying end groups, polyurethane silicone block copolymers, silicones, fluoropolymers, fluoroelastomers, polyethylenes, and polyesters.

18. The method of claim 1, wherein attaching the tubular electrode sub-assembly comprises welding the tubular electrode sub-assembly to the lead body.

19. The method of claim 1, wherein attaching the tubular electrode sub-assembly to the lead body comprises adhesively attaching the inner liner surface to the lead body.

* * * * *